(12) United States Patent
Houben et al.

(10) Patent No.: US 6,979,748 B2
(45) Date of Patent: Dec. 27, 2005

(54) METHOD FOR PREPARING AMINO ALKYL (METH)ACRYLATES

(75) Inventors: Jochen Houben, Kempen (DE); Ralph Eickwinkel, Nettetal (DE); Oliver Hoppe, Krefeld (DE); Bernd Kubiak, Krefeld (DE); Erich Kuester, Krefeld (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 164 days.

(21) Appl. No.: 10/311,600

(22) PCT Filed: Jun. 1, 2001

(86) PCT No.: PCT/EP01/06237

§ 371 (c)(1),
(2), (4) Date: Dec. 18, 2002

(87) PCT Pub. No.: WO01/98254

PCT Pub. Date: Dec. 27, 2001

(65) Prior Publication Data

US 2004/0092764 A1 May 13, 2004

(30) Foreign Application Priority Data

Jun. 21, 2000 (DE) ........................................ 100 29 517

(51) Int. Cl.$^7$ .............................................. C07C 69/52
(52) U.S. Cl. ..................... 560/205; 560/217; 560/156; 560/172
(58) Field of Search ................................ 560/205, 217

(56) References Cited

U.S. PATENT DOCUMENTS 4,281,175 A * 7/1981 Kametani et al. ........... 560/217
4,301,297 A * 11/1981 Kametani et al. ........... 560/217

FOREIGN PATENT DOCUMENTS

| DD | 152 540 | 12/1981 |
|---|---|---|
| DE | 27 25 255 | 12/1977 |
| DE | 27 52 109 | 6/1978 |
| EP | 0 118 639 | 9/1984 |
| EP | 0 160 427 | 11/1985 |
| EP | 0 906 902 | 4/1999 |
| EP | 0 960 877 | 12/1999 |
| JP | 5334714 | * 3/1978 |
| JP | 53 034714 | 3/1978 |

OTHER PUBLICATIONS

Otera et al., Chem. Rev. 1993, 93, 1449–1470.*
Orita et al., Tetrahedron (1999), 55(10), 2899–2910.*
J. Otera et al., "Distannoxane–catalysed Transesterification of 1,n–Diol Diacetates. Selective Transformation of Either of Chemically Equivalent Functional Groups", J. Chem. Soc., Chem. Commun., 1991, pp. 1742–1743.
J. Otera et al., "Distannoxane–Catalyzed Acetalization of Carbonyls", Tetrahedron vol. 48, No. 8, pp. 1449–1456, 1992.
J. Otera et al., "Novel Template Effects of Distannoxane Catalysts in Highly Efficient Transesterification and Esterification", J. Org. Chem., 1991, 56, pp. 5307–5311.
A. Orita et al., "Mild and Practical Acylation of Alcohols with Esters or Acetic Anhydride under Distannoxane Catalysis", Tetrahedron 55, 1999, pp. 2899–2910.
M. Pereyre et al., "Les alcoxytrialcoylétains, catalyseurs des réactions de transestérification", Bulletin de la Société Chimique de France, 1969, No. 1.
JP04–095054, N. Hideaki et al., Patent Abstracts of Japan, Mar. 27, 1992.
JP03–118352, K. Yukiya et al., Patent Abstracts of Japan, May 20, 1991.
JP04–066555, H. Akihiro et al., Patent Abstracts of Japan, Mar. 2, 1992.
JP03–181449, M. Kenji et al., Patent Abstracts of Japan, Aug. 7, 1991.
JP02–059546, K. Masahiro et al., Patent Abstracts of Japan, Feb. 28, 1990.
JP02–017155, K. Masahiro et al., Patent Abstracts of Japan, Jan. 22, 1990.
JP01–299263, N. Shinzo et al., Patent Abstracts of Japan, Dec. 4, 1999.
JP04–002830, T. Osamu et al., Patent Abstracts of Japan, Jan. 7, 1992.
Junzo Otera: "Transesterification" Chem. Rev., vol. 93, pp. 1449–1470 1993.

* cited by examiner

*Primary Examiner*—Johann R. Richter
*Assistant Examiner*—Karl Puttlitz
(74) *Attorney, Agent, or Firm*—Oblon, Spivak, McClelland, Maier & Neustadt, P.C.

(57) ABSTRACT

A process for the preparation of aminoalkyl (meth)acrylates by transesterification from $C_1$–$C_4$-alkyl (meth)acrylates and aminoalcohols is described, in which process the transesterification is carried out in the presence of at least one distannoxane of the general formula (1)

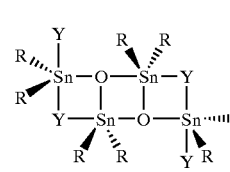

(1)

wherein
R=linear, cyclic or branched alkyl radical having from 1 to 6 carbon atoms, phenyl radical, and the radicals R may be identical or different from one another,
Y=halogen, preferably Cl, Br; pseudo-halogen, preferably SCN; OH, OAc or OR, the radicals Y being identical or different from one another,
as catalyst, and the use of the aminoalkyl(meth)acrylates prepared according to the process in the preparation of cationic monomers.

17 Claims, No Drawings

METHOD FOR PREPARING AMINO ALKYL (METH)ACRYLATES

The invention relates to an improved process for the preparation of aminoalkyl (meth)acrylates using distannoxanes as catalyst.

Aminoalkyl (meth)acrylates, such as, for example, dimethylaminoethyl acrylate and dimethylaminoethyl methacrylate, are very valuable as starting materials for cationic polymers, such as are used, for example, in flocculating agents. Both homopolymers and copolymers with other monomers may be used. The dimethylaminoethyl acrylate or the dimethylaminoethyl methacrylate may be used in the polymerisation directly or after quaternisation of the tertiary amino function. Such a quaternisation is usually carried out on a large scale using, for example, dimethyl sulfate or methyl chloride.

Owing to the basic nature of dimethylaminoalcohol, the preparation of dimethylaminoalkyl (meth)acrylate cannot be carried out by direct esterification but requires transesterification of the dimethylaminoalcohol with (meth)acrylic acid esters of short-chained alcohols.

In the preparation of acrylates in particular, but also to a lesser extent in the preparation of methacrylates, side reactions occur during the transesterification. Such side reactions are explained for the most part by the Michael addition of the alcohol that is freed or of the dimethylaminoalcohol to the dimethylaminoalkyl (meth)acrylate that forms or to the alkyl (meth)acrylate used as raw material. While the addition of the alcohol that is freed can be suppressed by suitable process-related measures, that is to say by rapid removal of the alcohol that forms, the same is not true in the case of dimethylaminoethanol. The ratio of the secondary products to the valuable product can be controlled, as well as via the reaction conditions, that is to say especially the reaction temperature, also to a large extent via the nature of the catalyst.

For economic reasons, a catalyst must be selective, highly active and re-usable. In addition, for reasons of better metering, a catalyst should be either liquid or readily soluble in the aminoalcohol. Solubility in the ethyl acrylate used as the transesterification component is not sufficient, since that substance has a flash point below room temperature and is suspected of causing permanent damage to health. Accordingly, for reasons of safety and cost, it is advantageous if the catalyst solution can be prepared and stored below the flash point, for example, of dimethylaminoethanol (39° C.) without the precipitation of solids occurring. Since re-use of the azeotropic mixture that is freed is indispensable for reasons of economy, it must also be required of a catalyst that, while being used for the intended purpose, it does not free any substances that build up in the boiling range of the azeotropic mixture.

The alkaline catalysts conventionally employed for transesterification, such as sodium methanolate, result in a large amount of Michael adduct, so that the resulting product discharged from the reactor can no longer be worked up economically to the target product.

In JP 90-405854 and JP 89-256222, the use of dibutyltin oxide is recommended for catalysing the transesterification of dimethylaminoethanol with methyl acrylate. That catalyst has the advantage of being very highly reactive, but it results in an increased amount of secondary products and, moreover, has the disadvantage that it is not soluble in dimethylaminoethanol or other aminoalcohols even in small amounts. As a result, its commercial use in batch preparation processes that permit the batchwise addition of solids to the starting materials is limited.

The use of acetyl acetonates of various transition metals as catalysts is recommended in a number of patents (JP 90-174549; JP 89-317700, JP 88-208221, JP 88-164874, JP 88-125971). Although such catalysts are very reactive, they have the disadvantage of cleaving acetylacetone in the reaction solution, which acetylacetone is disadvantageously found again in the azeotropic mixture and renders impossible its use, which is necessary for economic reasons, in the preparation of fresh alkyl(meth)acrylate.

Furthermore, such catalysts lose their activity very rapidly when used, which rules out their re-use and in some cases even requires the metering in of further catalyst in order to bring the reaction to an acceptable conversion.

Orthoethyl titanate, described in DE 38 74 827, catalyses the transesterification with ethyl acrylate very selectively but is markedly inferior to dibutyltin oxide in terms of reaction velocity. For that reason, either larger amounts of that catalyst must be employed or, alternatively, substantially longer reaction times must be accepted or relatively large excesses of alkyl acrylate must be used. Both are disadvantageous from the point of view of economy.

A further disadvantage of titanates is their ready hydrolysability, since traces of water are always introduced into the system by the starting materials, especially the hygroscopic aminoalcohol. For example, dimethylaminoethanol, which is commercially available, contains water in the order of magnitude of about 500 ppm. As a result of such traces of water, solid titanium dioxide forms which, on handling of the product discharged from the reactor or of the base residue of the distillation, leads to considerable wear of pipes and pumps. As a result of that hydrolysis, re-use of at least part of the base residue of the distillation, which is desirable for economic and ecological reasons, is possible only after expensive working up (filtration). Furthermore, tetraethyl titanate can be used only in the case of transesterification with ethyl acrylate, since it cleaves ethanol relatively rapidly in the reaction solution, which ethanol passes into the distillate that is to be recycled.

EP 118 639 and EP 160 427 describe an improved titanate-based catalyst, which is prepared by transesterification of tetraethyl titanate with dimethylaminoethanol. The catalyst so prepared may be used irrespective of the nature of the alkyl(meth)acrylate that is employed but, like tetraethyl titanate, it has the disadvantages of ready hydrolysability and low reactivity, which in turn leads to poor reusability of the base residue.

In JP 90-100727 there has been proposed a process for the preparation of dimethylaminoethyl acrylate from dimethylaminoethanol and methyl acrylate using Lipase M as the catalyst. That process has not cained acceptance, however.

Accordingly, the object of the invention was to provide a process for the preparation of aminoalkyl(meth)acrylates that permits an economical operating procedure particularly in a large-scale process, using one or more catalysts that do not exhibit the above-mentioned disadvantages of the prior art.

The object is achieved according to the invention by the transesterification of $C_1$–$C_4$-alkyl(meth)acrylates with aminoalcohols, the transesterification being carried out in the presence of at least one distannoxane of the general formula (1)

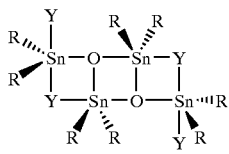

(1)

R=linear, cyclic or branched alkyl radical having from 1 to 6 carbon atoms, phenyl radical, the radicals R being identical or different from one another, Y=halogen, preferably Cl, Br; pseudo-halogen, preferably SCN; OH, OAc or OR, the radicals Y being identical or different from one another, as catalyst.

The catalytic mode of action of the class of substances of the distannoxanes has already been described in a number of articles. For example, acetals have been obtained in high yields from aldehydes using distannoxanes with a large excess of ethylene glycol (Tetrahedron 48, 1992, 1449–1456). It has also been found that the selectivity of distannoxanes in the saponification of acetates falls greatly as the difference between the functionalities increases (J. Chem. Soc., Chem. Commun., 1991, 1742–1743). It has also been possible to show that distannoxanes may also be used in the transesterification of carboxylic acid esters of low-boiling alcohols with high-boiling alcohols (J. Org. Chem. 1991, 56, 5307–5311). In those works, neither the use of a carboxylic acid or of a carboxylic acid ester having a double bond amenable to Michael addition nor the use of aminoalcohol as the transesterification component has been described.

It was surprising, therefore, that distannoxanes of the general formula (1) are suitable, or can be employed economically, as catalysts for the preparation of aminoalkyl (meth)acrylates, particularly in a large-scale commercial process, since Pereyre et al. (Bull. Soc. Chim. Fr. 1969, 262–263) have already described in relation to tributyltin alkoxides, which are chemically closely related to distannoxanes, that only unacceptable yields of from 30 to 70% have been obtained in the transesterification of acrylic acid esters.

The preparation of the distannoxanes of the general formula (1) according to the invention, which are obtainable inter alia in a simple manner by reaction of organotin oxide compounds with the corresponding organotin halide compounds, is described in the literature (Chem. Rev. 1993, 93, 1449–1470 and literature cited therein).

Preferred distannoxanes are diisopropyldibutyltetrachlorodistannoxane, diisopropyldimethyltetrachlorodistannoxane, dibutyldioctyltetrachlorodistannoxane, dimethyldioctyltetrachlorodistannoxane and dimethyldibutyltetrachlorodistannoxane, which may be used in the process preferably alone or, alternatively, in the form of a catalyst mixture. The amount of catalyst used is from 0.1 to 10 mmol, preferably from 0.2 to 1 mmol, per mol of aminoalcohol. Octabutyltetrachlorodistannoxane (R=n-butyl, Y=Cl) is preferably used as the catalyst.

Suitable aminoalcohols according to the invention are all tertiary amines that have at least one primary alcohol function, such as dialkylmonoalkanolamines, monoalkyldialkanolamines or trialkanolamines, wherein alkyl may be a linear or branched alkyl radical having $C_1$–$C_{22}$ carbon atoms and alkanol may be ethanol or propanol. Of the group of the dialkylmonoalkanolamines there may be mentioned preferably, but not conclusively: dimethylaminoethanol, dimethylaminopropanol, diethylaminoethanol, diethylaminopropanol, 3-(dimethylamino)-2,2-dimethyl-1-propanol. Of the group of the monoalkyldialkanolamines there may be mentioned by way of example, but not exclusively, N-methyldiethanolamine or $C_{12}$–$C_{14}$-diethanolamine, and as trialkanolamines triethanolamine.

The $C_1$–$C_4$-alkyl(meth)acrylates used according to the invention are, for example but not exclusively, methyl acrylate, methyl methacrylate, ethyl acrylate, isopropyl acrylate or n-butyl acrylate, with ethyl acrylate being preferred.

In the preparation process, the alkyl ester, with the exception of isopropyl acrylate ester, is preferably used in a stoichiometric excess, since a certain proportion is discharged azeotropically in the distillate with the alcohol that forms. The stoichiometric excess to be used is to be chosen differently in dependence on the alkyl radical according to the position of the azeotropic mixture, as a result of which, for example, in the case of methyl acrylate, a larger excess is to be used than in the case of ethyl acrylate. The position of the azeotropic mixtures that are theoretically to be achieved can be determined by experiment or taken from relevant standard works (e.g. Advances in Chemistry Series 116, Azeotropic Data-III). In a commercial layout, distilling off of the azeotropic mixture that is theoretically to be achieved at normal pressure with 72.7% ethanol, for example in the case of ethyl acrylate, will often be dispensed with for economic reasons; instead, while optimising costs in terms of the theoretical number of plates and the reflux ratio, a mixture will be drawn off with from 65 to 70% ethanol.

The transesterification reaction is able to take place at low temperatures, such as, for example, room temperature, but, without removal of the resulting short-chained alcohol by distillation, leads to an equilibrium that is predominantly on the side of the starting materials. Likewise, at low temperatures relatively long times are required for the attainment of equilibrium, and/or relatively large and hence uneconomical amounts of catalyst. On the other hand, low reaction temperatures, with overall conditions otherwise the same, have a positive effect on the selectivity of the reaction. Accordingly, the reaction is preferably carried out at from 60 to 180° C., the reaction taking place at a pressure in the range from 100 to 1100 mbar, preferably at a pressure in the range from 400 to 1100 mbar.

There are used as polymerisation inhibitors according to the invention conventional inhibitors, such as, for example, phenothiazine, tert-butylcatechol, hydroquinone monomethyl ether, hydroquinone, methylene blue, copper sulfate, iron sulfate, alone or in the form of an inhibitor mixture, in an amount of from 250 to 5000 ppm, preferably from 250 to 2500 ppm, with an amount of 1000 ppm, based on the total batch, being particularly preferred.

On a commercial scale, the reaction may be carried out batchwise, semi-batchwise or continuously. For economic reasons, attempts will always be made to make the process fully continuous when higher annual productions of an alkylamino (meth)acrylate are sought.

Where the reaction and working up are carried out batchwise, there is the disadvantage that the high boilers that are formed, which are especially Michael addition products, decompose again under the relatively prolonged thermal load and release low-boiling starting materials which then contaminate the valuable product. Of the low-boiling impurities, the readily volatile(meth)acrylic acid esters used as starting materials are especially disadvantageous, since they are not converted in the subsequent alkylation and accordingly substantially increase the potential danger coming from the aqueous monomer solution as a result of their odour and owing to their negative toxicological properties and their low flash point. The formation of low-boiling cleavage products can be avoided by, after the reaction, first separating the reactor discharge product from the high boilers by gentle distillation—e.g. by means of a falling-film or thin-layer evaporator—wherein the residence time under a thermal load is less than 10 minutes, and only then subjecting it to fractional distillation to purify the valuable product.

In a preferred embodiment of the process, in the above-mentioned continuous working up, the high boilers are first separated off in a distillation step in which the residence time under a thermal load is less than 5 minutes, particularly preferably less than one minute.

In the case of the continuous form of the reaction, it is possible both to carry out the reaction in a continuous-flow reactor with a column mounted thereon or, advantageously, to arrange one or more similarly constructed reactors downstream of that first reactor, in order to achieve higher conversions in the reaction or, in the optimum case, even to achieve complete conversion. It may be expedient from a technical point of view to operate those reactors at the same temperature level but at different pressure levels, the pressure being reduced from reactor to reactor. It is also possible to conduct the reaction in a reactive column, wherein the starting material mixture is fed in at the middle and the low-boiling alcohol that forms leaves the column as an azeotropic mixture via the head of the buoyancy section, while the converted reaction mixture containing the valuable product is removed at the foot of the stripping section. The trained installation constructor may provide a buffer tank of suitable dimensions between the continuously operated reaction part and working up, which is likewise operated continuously.

In a preferred embodiment of the process, the aminoalkyl (meth)acrylates that are prepared are worked up in a continuous distillation process, and the low-boiling fraction that forms is fed back into the reaction.

In a further embodiment, from 1 to 100%, preferably from 25 to 95%, particularly preferably from 50 to 90%, of the base fraction that forms is fed back into the reaction.

The aminoalkyl(meth)acrylates, in particular dimethylaminoethyl acrylate and dimethylaminoethyl methacrylate, prepared by the process according to the invention are used in the preparation of cationic monomers.

The distannoxanes of the general formula (1) used as catalysts in the process according to the invention have none of the disadvantages associated with the other catalysts known from the prior art. In particular, they exhibit a higher selectivity than the catalysts used hitherto and an equal level of reactivity as dibutyltin oxide. Since they do not lose their activity even in the presence of amounts of water that are usual in the process, the base residue of the distillation can be recycled without pretreatment, in contrast to reactions with titanate catalysis. A further advantage is their low toxicity. Octabutyltetrachlorodistannoxane in particular, in contrast to the corresponding dibutyltin oxide, is soluble in alkylaminoethanol in concentrations of over 10% even at room temperature, which permits problem-free metering into the reactor.

EXPERIMENTAL SECTION

EXAMPLE 1

Preparation of the Catalyst Octabutyltetrachlorodistannoxane 250 g of n-heptane are introduced into a stirred reactor, and 24.89 g of dibutyltin oxide and 30.80 g of dibutyltin dichloride are added. The batch is stirred for 16 hours at room temperature (RT), following which the solid (dibutyltin oxide) present at the beginning has dissolved almost completely. The small amount of solid still present is filtered off, and concentration is carried out to a volume of 100 ml. The solid that precipitates on cooling is filtered off with suction and dried for 2 hours at 70° C. in a circulating-air drying cabinet. Yield 54 g=97% of the theoretical yield.

EXAMPLE 2

Solubility of the Catalyst

A mixture of 12 wt. % of the catalyst according to the invention of Example 1 and 88 wt. % of dimethylaminoethanol was mixed and stirred for one hour at 38° C. A clear solution that was free of solids was obtained.

COMPARISON EXAMPLE 1

Poor Solubility of Dibutyltin Oxide

A mixture of 5 wt. % dibutyltin oxide and 95 wt. % dimethylaminoethanol was stirred first for 3 hours at RT and then for 3 hours at 39° C. The dibutyltin oxide did not dissolve in the dimethylaminoethanol.

A mixture of 2.5 wt. % dibutyltin oxide and 97.5 wt. % dimethylaminoethanol was stirred first for 3 hours at RT and then for 3 hours at 39° C. The dibutyltin oxide did not dissolve in the dimethylaminoethanol.

The same tests were carried out 10% in ethanol and 10% in ethyl acrylate. A solution could not be obtained in either case.

EXAMPLE 3

Preparation of the Catalyst Diisopropyldibutyltetrachlorodistannoxane 1.04 g of diisopropyltin oxide and 1.43 g of dibutyltin dichloride are stirred for two days in 50 ml of toluene in a 100 ml round-bottomed flask. Once the batch has turned into a clear solution, 30.1 g of toluene are distilled off via a distillation bridge. The solid that precipitates is filtered off on a Buchner funnel and then finely distributed in a Petri dish and dried for 72 hours in a conventional laboratory hood.

EXAMPLE 4

Preparation of the Catalyst Diisopropyldimethyltetrachlorodistannoxane 1.24 g of diisopropyltin oxide and 1.23 g of dimethyltin dichloride are stirred for two days in 50 ml of toluene in a 100 ml round-bottomed flask. Once the batch has turned into a clear solution, 27.5 g of toluene are distilled off via a distillation bridge. The solid that precipitates is filtered off on a Buchner funnel and then finely distributed in a Petri dish and dried for 72 hours in a conventional laboratory hood.

EXAMPLE 5

Preparation of Dibutyldioctyltetrachlorodistannoxane

Dibutyldioctyltetrachlorodistannoxane is prepared analogously to Example 4 from dibutyltin dichloride and dioctyltin oxide in n-heptane.

EXAMPLE 6

Preparation of Dimethyldioctyltetrachlorodistannoxane

Dimethyldioctyltetrachlorodistannoxane is prepared analogously to Example 4 from dimethyltin dichloride and dioctyltin oxide in n-heptane.

EXAMPLE 7

Preparation of Dimethyldibutyltetrachlorodistannoxane

Dimethyldibutyltetrachlorodistannoxane is prepared analogously to Example 4 from dimethyltin dichloride and dibutyltin oxide in n-heptane.

Transesterifications

The syntheses were carried out in a one-liter glass flask with a rapidly rotating glass stirrer D/D=⅓. Heating was by means of a controlled oil bath. The vapours were passed over a packed column having six theoretical plates (determined using a n-hexane/n-heptane test mixture) and packed with stainless-steel wire nets (diameter 6 mm) from MSM, onto a controlled column head in which the alcohol formed as the reaction coupling product was removed in its respective azeotropic mixture. According to the (meth)acrylic acid esters used, the operation was carried out with or without a vacuum, as desired, and with different reflux ratios according to the separating function. The distillate and the base product were analysed by gas chromatography.

EXAMPLE 8

193.6 g (2.17 mol) of dimethylaminoethanol, 206.4 g (1.61 mol) of butyl acrylate, 0.5 g of phenothiazine and 1.25 g of the catalyst prepared according to Example 1 were placed together and heated to a base temperature of 125° C. The internal pressure of the apparatus was lowered in the course of the reaction from 700 to 400 mbar. The removal ratio at the head of the column was set at 1:10. 128.1 g of distillate were removed in the course of 15 hours. The base residue had the following composition:

| n-butanol | 0.82 wt. % |
| dimethylaminoethanol | 16.75 wt. % |
| n-butyl acrylate | 7.85 wt. % |
| dimethylaminoethyl acrylate | 68.76 wt. % |
| higher-boiling impurities | 5.82 wt. % |
| selectivity | 91.5% |

EXAMPLE 9

203.2 g (2.28 mol) of dimethylaminoethanol, 296.8 g (2.97 mol) of ethyl acrylate, 0.5 g of phenothiazine and 1.25 g of the catalyst prepared according to Example 1 were placed together at normal pressure and heated to a base temperature of 137° C. in the course of seven hours. 97.3 g of distillate passed over at a reflux ratio of 1:7 and a head temperature of 77.8–78° C. The base residue had the following composition:

| ethanol | 0.51 wt. % |
| ethyl acrylate | 14.27 wt. % |
| dimethylaminoethanol | 7.71 wt. % |
| dimethylaminoethyl acrylate | 76.62 wt. % |
| higher-boiling impurities | 0.89 wt. % |
| selectivity | 98.83% |

COMPARISON EXAMPLE 2

The procedure of Example 9 was followed but, instead of the catalyst according to the invention, the same amount of dibutyltin oxide was used. The base residue had the following composition:

| ethanol | 0.15 wt. % |
| ethyl acrylate | 4.19 wt. % |
| dimethylaminoethanol | 6.90 wt. % |
| dimethylaminoethyl acrylate | 84.79 wt. % |
| higher-boiling impurities | 3.72 wt. % |
| selectivity | 95.6% |

It is clear that the amount of higher-boiling impurities is markedly higher than in Example 9 according to the invention.

EXAMPLE 10

Re-Use of the Base Residue of the Distillation and Distillate

The product of Example 9 was distilled at 100 mbar over a packed column having six theoretical plates. Distillate 2 (6.3% ethanol; 57.5% ethyl acrylate; 28.6% dimethylaminoethanol (DMAE); 7.6% dimethylaminoethyl acrylate) formed to a head temperature of 90° C. (reflux ratio 1:5) was saved for re-use. The base residue obtained after distillation of the valuable product to a head temperature of 102° C. (reflux 4:2) was likewise kept for re-use. In four successive batches, in each case ¾ of the base residue of the distillation that had been obtained and the whole of distillate 2 that had been obtained were re-used. Full account was taken in the batch of the amount of ethyl acrylate and DMAE contained in distillate 2, and the amount of freshly used catalyst was reduced to ⅓ and the polymerisation inhibitor to 40% as compared with Example 4, without the reaction velocity falling or the polymerisation tendency increasing as a result.

EXAMPLE 11

128.2 g (1.44 mol) of dimethylaminoethanol, 371.8 g (4.32 mol) of methyl acrylate, 0.5 g of phenothiazine and 1.25 g of the catalyst prepared according to Example 1 were placed together at normal pressure and heated to 100° C. in the course of 5 hours at a reflux ratio of 1:3. The distillate was removed at a head temperature of 65° C. at normal pressure.

The base residue had the following composition:

| methanol | 0.25 wt. % |
| methyl acrylate | 35.74 wt. % |
| dimethylaminoethanol | 12.55 wt. % |
| dimethylaminoethyl acrylate | 51.00 wt. % |
| higher-boiling impurities | 0.46 wt. % |
| selectivity | 99.1% |

EXAMPLE 12

168.8 g of N-methyl-2,2-iminodiethanol and 713.3 g of methyl acrylate were placed together at normal pressure with 0.9 g of phenothiazine and 4.5 g of the catalyst of Example 1, and esterified. When the reaction was complete, the contents of the reactor had the following composition:

| | |
|---|---|
| methanol | 0.28 wt. % |
| methyl acrylate | 36.44 wt. % |
| N-methyldiethanolamine | 0.08 wt. % |
| monoester | 1.72 wt. % |
| N-methyl-2,2-iminodiethyl diacrylate | 58.06 wt. % |
| higher-boiling impurities | 1.22 wt. % |
| selectivity | 97.9% |

The product discharged from the reactor was first freed of low boilers at 10 mbar/70° C. and then distilled at 0.3 mbar and a base temperature of 120° C. The resulting water-clear product was stabilised with 1000 ppm of hydroquinone monomethyl ether.

EXAMPLE 13

5 liters of a reactor discharge product prepared according to Example 8 were fed into a continuous distillation apparatus at a feed rate of 350 g/h. The first part of the continuous distillation apparatus consisted of a packed buoyancy column having an inside diameter of 30 mm and a separation efficiency of 4 theoretical plates, and a stripper column packed with stainless-steel packing and having an inside diameter of 40 mm and six theoretical plates. The low boilers were removed over a column head controlled according to temperature and reflux ratio. The resulting base residue was introduced continuously into a thin-layer evaporator, the vapours of which were passed to the foot of a packed column having five theoretical plates (reflux ratio 1:1) and the head of which was cooled to 0° C. by means of a circulating cooler. The colourless valuable product was obtained at the head of that column in a purity of 99.97% and was stabilised with 1000 ppm of hydroquinone monomethyl ether. The distillate obtained at the head of the first column (4.12% ethanol, 64.96% ethyl acrylate, 27.72% dimethylaminoethanol (DMAE), 3.18% dimethylaminoethyl acrylate) could be used again in the reaction.

EXAMPLE 14

Quaternisation of Dimethylaminoethyl Acrylate 858 g of the dimethylaminoethyl acrylate prepared in Example 13 were introduced together with 291 g of deionised water into a 2-liter autoclave from Juchheim. The stirring speed was adjusted to 275 rpm and the contents of the reactor were heated to 50° C. At that temperature, the metering in of methyl chloride was begun and was complete after 28 minutes, the internal temperature being prevented from rising above 70° C. by cooling by means of a thermostat. The methyl chloride taken from a compressed gas cylinder was monitored by continuously weighing the compressed gas cylinder. 301.5 g of methyl chloride=99.5% of theory were taken up. A clear colourless liquid having a water content of 20% was obtained.

EXAMPLE 15

Polymerisation of the Resulting Cationic Monomer

The product of Example 14 was polymerised analogously to Example 12 of EP 374 458 and tested as described in Example 1 of that EP. The results were comparable with those of the dimethylaminoethyl acrylate sold by Elf Atochem under the name "ADAME".

EXAMPLE 16

236.9 g (2.66 mol) of diethylaminoethanol, 263.1 g (2.63 mol) of ethyl acrylate, 0.5 g of phenothiazine and 1.25 g of the catalyst prepared according to Example 1 were placed together at normal pressure and heated to a base temperature of 132° C. in the course of 5 hours at a reflux ratio of 1:7. Distillate passed over at a head temperature of 77–78° C.

The base residue had the following composition:

| | |
|---|---|
| ethanol | 0.84 wt. % |
| ethyl acrylate | 15.25 wt. % |
| diethylaminoethanol | 12.88 wt. % |
| diethylaminoethyl acrylate | 70.19 wt. % |
| higher-boiling impurities | 0.64 wt. % |
| selectivity | 99.10% |

EXAMPLE 17

236.9 g (2.66 mol) of diethylaminoethanol, 263.1 g (2.63 mol) of ethyl acrylate, 0.5 g of phenothiazine and 1.25 g of the catalyst prepared according to Example 3 were placed together at normal pressure and heated to a base temperature of 132.3° C. in the course of 5 hours at a reflux ratio of 1:7. Distillate passed over at a head temperature of 77–78° C.

The base residue had the following composition:

| | |
|---|---|
| ethanol | 0.29 wt. % |
| ethyl acrylate | 15.95 wt. % |
| diethylaminoethanol | 16.12 wt. % |
| diethylaminoethyl acrylate | 66.33 wt. % |
| higher-boiling impurities | 1.16 wt. % |
| selectivity | 98.30% |

EXAMPLE 18

236.9 g (2.66 mol) of diethylaminoethanol, 263.1 g (2.63 mol) of ethyl acrylate, 0.5 g of phenothiazine and 1.25 g of the catalyst prepared according to Example 4 were placed together at normal pressure and heated to a base temperature of 138.8° C. in the course of 6 hours at a reflux ratio of 1:7. Distillate passed over at a head temperature of 77–78° C.

The base residue had the following composition:

| | |
|---|---|
| ethanol | 0.73 wt. % |
| ethyl acrylate | 9.77 wt. % |
| diethylaminoethanol | 12.11 wt. % |
| diethylaminoethyl acrylate | 75.11 wt. % |
| higher-boiling impurities | 2.09 wt. % |
| selectivity | 97.30% |

EXAMPLE 19

203.4 g (2.29 mol) of diethylaminoethanol, 296.6 g (2.97 mol) of ethyl acrylate, 0.5 g of phenothiazine and 1.25 g of the catalyst prepared according to Example 5 were placed together at normal pressure and heated to a base temperature of 140.5° C. in the course of 6 hours at a reflux ratio of 1:7. Distillate passed over at a head temperature of 77–78° C.

The base residue had the following composition:

| | |
|---|---|
| ethanol | 0.59 wt. % |
| ethyl acrylate | 9.52 wt. % |
| diethylaminoethanol | 10.97 wt. % |
| diethylaminoethyl acrylate | 76.87 wt. % |
| higher-boiling impurities | 1.88 wt. % |
| selectivity | 97.60% |

EXAMPLE 20

203.4 g (2.29 mol) of diethylaminoethanol, 296.6 g (2.97 mol) of ethyl acrylate, 0.5 g of phenothiazine and 1.25 g of the catalyst prepared according to Example 6 were placed together at normal pressure and heated to a base temperature of 140.1° C. in the course of 6 hours at a reflux ratio of 1:7. Distillate passed over at a head temperature of 77–78° C.

The base residue had the following composition:

| | |
|---|---|
| ethanol | 0.52 wt. % |
| ethyl acrylate | 10.37 wt. % |
| diethylaminoethanol | 14.32 wt. % |
| diethylaminoethyl acrylate | 72.14 wt. % |
| higher-boiling impurities | 1.88 wt. % |
| selectivity | 96.70% |

EXAMPLE 21

203.4 g (2.29 mol) of diethylaminoethanol, 296.6 g (2.97 mol) of ethyl acrylate, 0.5 g of phenothiazine and 1.25 g of the catalyst prepared according to Example 7 were placed together at normal pressure and heated to a base temperature of 139.5° C. in the course of 6 hours at a reflux ratio of 1:7. Distillate passed over at a head temperature of 77–78° C.

The base residue had the following composition:

| | |
|---|---|
| ethanol | 0.81 wt. % |
| ethyl acrylate | 9.16 wt. % |
| diethylaminoethanol | 13.12 wt. % |
| diethylaminoethyl acrylate | 73.99 wt. % |
| higher-boiling impurities | 2.73 wt. % |
| selectivity | 96.44 wt. % |

EXAMPLE 22

Working up of the Product Discharged from the Reactor

A reactor discharge product containing 3.05 wt. % high boilers was first passed over a thin-layer evaporator of type DVS2VA from QVF at 17 mbar, a heat carrier temperature of 105° C. and a feed rate of 25 g per minute, there resulting a head temperature of 66° C.

The distillate was collected in a flask containing 1000 ppm of hydroquinone monomethyl ether (HQME), and had the following composition:

| | |
|---|---|
| ethanol | 0.02 wt. % |
| ethyl acrylate | 2.20 wt. % |
| dimethylaminoethanol | 2.13 wt. % |
| dimethylaminoethyl acrylate | 95.46 wt. % |
| higher-boiling impurities | 0.10 wt. % |

The distillate was distilled in a batch distillation under a vacuum of 100 mbar over a column having 6 theoretical plates. The first runnings were removed to a head temperature of 90° C. at a reflux ratio of 5. The receiver was then exchanged for a fresh flask containing 1000 ppm hydroquinone monomethyl ether, and the product dimethylaminoethyl acrylate was obtained in a purity of 99.99% at a head temperature of 102° C. and a removal ratio of 4:2.

What is claimed is:

1. A process for producing aminoalkyl (meth)acrylates, comprising:
   transesterifying one or more $C_1$–$C_4$-alkyl (meth)acrylates and one or more aminoalcohols in the presence of a catalytically effective amount of at least one distannoxane of formula (1):

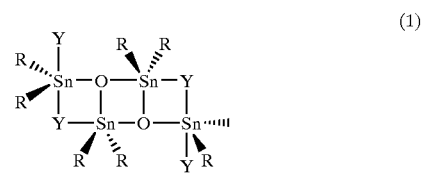

to form one or more aminoalkyl (meth)acrylates,
wherein
   each Y is, independently, a halogen, SCN, OH, OAc or OR, and
   each R is, independently, a linear, cyclic or branched alkyl radical having from 1 to 6 carbon atoms or phenyl radical.

2. The process according to claim 1, wherein said at least one distannoxane is selected from the group consisting of diisopropyldibutyltetrachlorodistannoxane, diisopropyldimethyltetrachlorodistannoxane, dibutyldioctyltetrachlorodistannoxane, dimethyldioctyltetrachlorodistannoxane, dimethyldibutyltetrachlorodistannoxane and octabutyltetrachlorodistannoxane.

3. The process according to claim 1, wherein the distannoxane is octabutyltetrachlorodistannoxane.

4. The process according to claim 1, wherein the distannoxane is present in an amount of from 0.1 to 10 mmol, per mol of aminoalcohol.

5. The process according to claim 1, wherein the aminoalcohols are dialkylaminoalcohols.

6. The process according to claim 5, wherein the dialkylaminoalcohol is selected from the group consisting of dimethylaminoethanol, dimethylaminopropanol, diethylaminoethanol and diethylaminopropanol.

7. The process according to claim 1, wherein the transesterification is carried out in the presence of one or more polymerization inhibitors.

8. The process according to claim 7, wherein the polymerization inhibitor is phenothiazine.

9. The process according to claim 1, wherein the transesterification takes place at a pressure in the range from 100 to 1100 mbar.

10. The process according to claim 1, further comprising working-up the aminoalkyl (meth)acrylates in a continuous distillation process to produce a low-boiling fraction, and feeding back the low-boiling fraction.

11. The process according to claim 10, in which is base fraction produced and wherein from 1 to 100% of the base fraction is fed back into the transesterification.

12. The process according to claim 10, wherein in the continuous working up, high-boiling components are first separated off in a distillation step in which the residence time under a thermal load is less than 10 minutes.

13. The process according to claim 1, wherein Y is Cl or Br.

14. The process according to claim 1, wherein the distannoxane present in an amount of from 0.2 to 1 mmol per mol of aminoalcohol.

15. The process according to claim 10, wherein from 25 to 95% of a base fraction is fed back into the reaction.

16. The process according to claim 10, wherein from 50 to 90% of a base fraction is fed back into the reaction.

17. The process according to claim 10, wherein in the continuous working up, the high-boiling components are first separated off in a distillation step in which the residence time under a thermal load is less than 1 minute.

* * * * *